United States Patent [19]

Ward

[11] 4,009,097
[45] Feb. 22, 1977

[54] SEPARATION PROCESS
[75] Inventor: Dennis J. Ward, South Barrington, Ill.
[73] Assignee: UOP Inc., Des Plaines, Ill.
[22] Filed: Nov. 20, 1975
[21] Appl. No.: 633,888

Related U.S. Application Data
[63] Continuation-in-part of Ser. No. 453,656, March 21, 1974, abandoned.
[52] U.S. Cl. .............................. 208/342; 208/101; 208/341
[51] Int. Cl.$^2$ ......................................... C10G 5/04
[58] Field of Search ................... 208/341, 342, 101

[56] References Cited
UNITED STATES PATENTS

| | | | |
|---|---|---|---|
| 2,181,302 | 11/1939 | Keith et al. | 208/101 |
| 2,596,785 | 5/1952 | Nelly et al. | 208/341 |
| 3,574,089 | 4/1971 | Forbes | 208/341 |

*Primary Examiner*—Herbert Levine
*Attorney, Agent, or Firm*—James R. Hoatson, Jr.; Robert W. Erickson; William H. Page, II

[57] ABSTRACT

Process with improved efficacy for the separation and recovery of desired liquid and vapor constituents from a feed stream containing such constituents. The feed stream is contacted with two separate and distinct lean oils by upward passage through an absorption zone. Resultant rich oil passes to a stripping zone and then to a fractionation zone. A first lean oil is withdrawn from fractionation zone bottoms and enters the absorption zone superior to the entry of a second lean oil. The second lean oil is withdrawn from the stripping zone and passed to the absorption zone. A stripped vapor is withdrawn from the stripping zone and is mixed with the feed. This mixture is partially condensed in a cooling zone and then separated into liquid and vapor phases in a separation zone. The vapor phase is then withdrawn from the separation zone and is introduced adjacent the lowermost point of the absorption zone. The liquid phase is withdrawn from the separation zone and is introduced into the absorption zone at an elevation superior to that of the introduction of the vapor phase.

3 Claims, 1 Drawing Figure

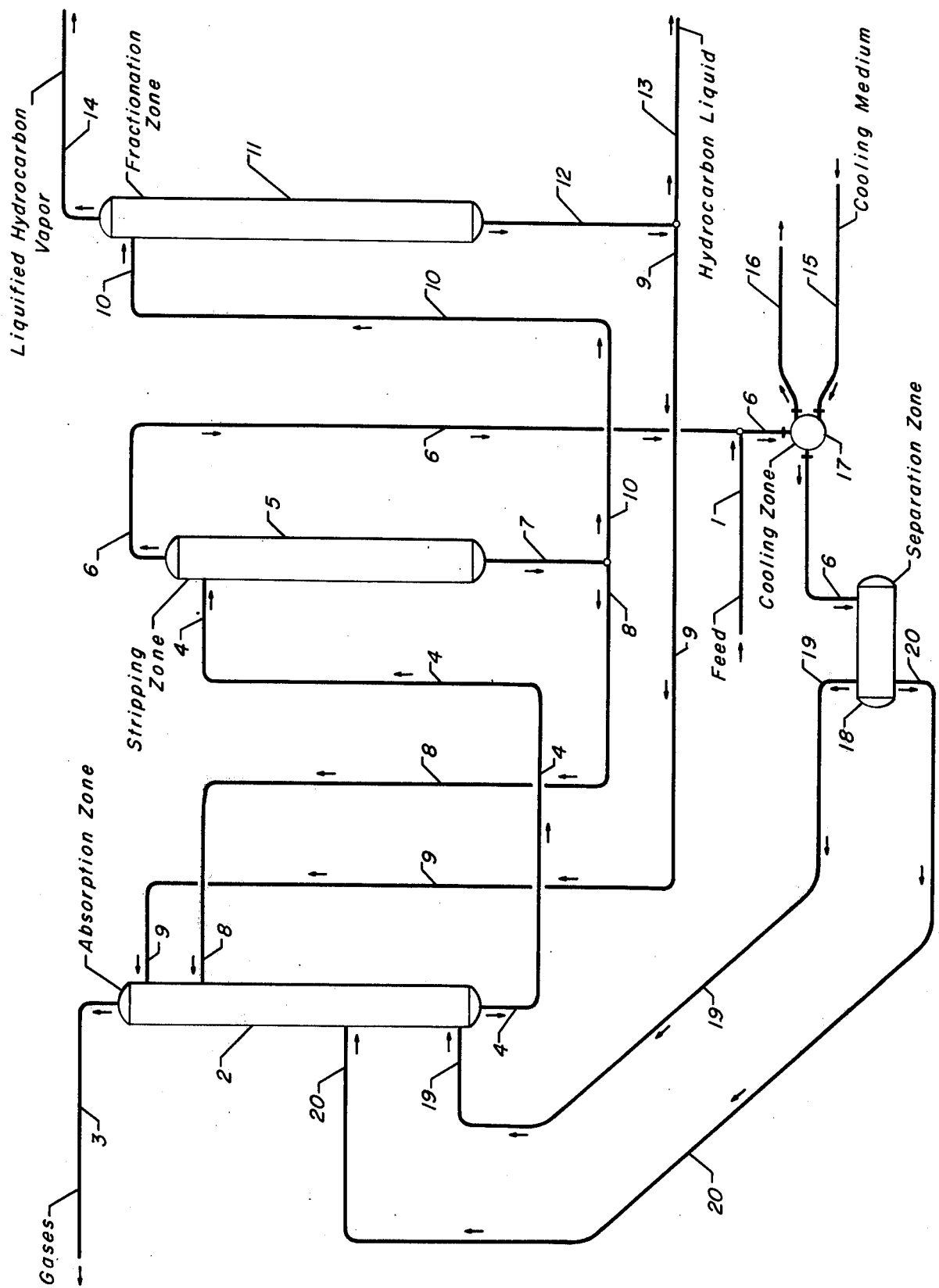

SEPARATION PROCESS

CROSS-REFERENCE TO RELATED APPLICATION

This application is a continuation-in-part of my co-pending application Ser. No. 453,656, filed Mar. 21, 1974, now abandoned.

BACKGROUND OF THE INVENTION

1. Field of the Invention

The field of art to which this invention pertains is hydrocarbon processing. It particularly relates to the recovery of desired liquid and vaporous constituents from a hydrocarbonaceous liquid-vapor feed stream. Specifically, this invention relates to the recovery of LPG and stabilized gasoline in an improved separation process.

2. Prior Art

Hydrocarbons which are vaporous at normal conditions are employed in the synthesis of many organic compounds. Ethylene, for example, is in demand as a starting material in the synthesis of alcohols and synthetic rubber. Propylene and butylenes are in particularly great demand for plastics manufacture and for conversion to high octane motor fuel blending components by polymerization and alkylation processes.

Sources of these vaporous hydrocarbons are petroleum cracking and conversion processes such as thermal cracking, catalytic cracking, reforming, hydrocracking, etc. The chemical reactions occurring in these processes produce commercially desirable quantities of vaporous hydrocarbons, and because of their utility it is desirable to recover them in as high a concentration as possible. For this reason, separation processes are commonly used to concentrate and recover these hydrocarbons.

Prior art separation processes, such as that described in U.S. Pat. No. 2,181,302, are comprised of three major sections or zones: absorption, stripping and fractionation. In essence, these zones serve, respectively, to absorb all but the lightest gaseous components, strip dissolved gases from the absorbed components, and fractionate the absorbed components into various product streams. An outstanding feature of these processes is that usually the heavier components in the feed to the process are suitable for use as an absorber oil in the absorption zone. A portion of the product stream containing these components is recycled back to the absorption zone. I have discovered an improvement which significantly improves the efficiency of such hydrocarbon separation processes.

OBJECTS AND EMBODIMENTS

It is an object of this invention to provide an improved method for the separation of hydrocarbons.

It is another object of this invention to provide a method for separating a liquid-vapor hydrocarbonaceous mixture into normally vaporous products and normally liquid products in a more efficacious manner. In one embodiment, my invention affords in a process for the recovery of selected hydrocarbon liquid and vapor constituents from a feed stream containing those constituents wherein (i) the feed stream passes upwardly through an absorption zone and contacts primary and secondary lean oils therein; (ii) a rich oil taken from the lowermost point of the absorption zone passes to a stripping zone; (iii) a stripped oil from the stripping zone passes to a fractionation zone and a stripped vapor from the stripping zone is intermixed with said feed stream and introduced into said absorption zone therewith; (iv) a portion of a fractionation zone bottoms stream is returned to the absorption zone as said secondary lean oil; and, (v) a portion of said stripped oil is returned to said absorption zone as said primary lean oil, The Improvement Which Comprises: (vi) introducing the mixture of stripped vapor and feed into a cooling zone and therein withdrawing heat from said mixture sufficient to cause partial condensation thereof; (vii) passing the partially condensed mixture of feed and stripped vapor from step (vi) to a separation zone and therein separating the mixture into liquid and vapor phases; (viii) withdrawing said vapor phase from the separation zone of step (vii) and introducing said vapor phase into said absorption zone adjacent said lowermost point thereof; and, (ix) withdrawing said liquid phase from the separation zone of step (vii) and introducing said liquid phase into said absorption zone above the vapor phase of step (viii).

BRIEF SUMMARY OF THE INVENTION

The present invention involves a process for the recovery of normally vaporous and normally liquid hydrocarbonaceous components from a composite stream containing these components, such as an effluent stream from a hydrocarbon conversion zone.

Lean oils absorb normally vaporous components from the composite stream in an absorption zone. Resulting rich oil passes to a stripping zone where light gases dissolved in the rich oil are removed and a stripped oil is produced. A first portion of the stripped oil is returned to the absorption zone as a lower lean oil; the remaining portion of stripped oil passes to a fractionation zone. The fractionation zone provides a liquefied hydrocarbon vapor product and a hydrocarbon liquid product. A portion of the hydrocarbon liquid product is returned to the absorption zone as an upper lean oil. The provision and juxtaposition of the upper and lower lean oils improves recovery of light feed components.

Stripped vapor withdrawn from the stripping zone is intermixed with incoming feed. The resulting admixture passes to a cooling zone where withdrawal of heat effects partial condensation of the mixture's components. The partially condensed mixture then passes to a separation zone where phase separation takes place. The vapor phase separated from the mixture is introduced into the bottom of the absorption zone, and the liquid phase is introduced into the absorption zone at a higher elevation. The provision of the cooling zone, the separation zone and the unique juxtaposition of entry of liquid and vapor phases into the absorption zone provides increased liquid-vapor contact and improved recovery of components which are desired to be recovered from the stripped vapor.

BRIEF DESCRIPTION OF THE DRAWING

An embodiment of the present invention is illustrated in the attached drawing. Only such details are included as are necessary for a clear understanding of my invention, and no intention is thereby made to unduly limit its scope. Unnecessary items such as certain process streams, valves, pumps, instrumentation and other equipment have been omitted for the sake of simplicity.

Referring now to the separation process shown in the drawing, a feed stream comprising hydrogen, normally vaporous hydrocarbons such as methane, ethane, propane, etc., and normally liquid hydrocarbons such as pentane, hexane, etc. enters the process through conduit 1. Feed entering in conduit 1 passes the conduit 6 and mixes with components situated therein, which components shall be hereinafter described. The resultant mixture passes in conduit 6 to cooling zone 17. A cooling medium, such as cold water, enters cooling zone 17 in conduit 15 and absorbs heat from the mixture therein contained and exits the cooling zone in conduit 16. Withdrawal of heat by the cooling medium from the contents of the cooling zone results in partial condensation of the mixture. The partially condensed mixture, now in the form of a liquid-vapor, two-phase stream, exits cooling zone 17 in conduit 16 and passes to separation zone 18. Phase separation takes place within the separation zone, permitting a vapor phase and a liquid phase to be separately withdrawn therefrom. The vapor phase exits separation zone 18 in conduit 19 and passes to the bottom of absorption zone 2. The liquid phase from separation zone 18 exits in conduit 20 and passes to a point of introduction to the absorption zone which is located above the point of introduction of conduit 19.

A first lean oil enters an upper part of absorption zone 2 in conduit 8. A second lean oil enters absorption zone 2 from conduit 9 above the entry point of the first lean oil. These lean oils pass downwardly through absorption zone 2, absorbing at least a portion of the vaporous hydrocarbon components of the feed. Gases not absorbed by the lean oil exit absorption zone 2 in conduit 3. A rich oil stream, containing liquid feed components, lean oils and absorbed gaseous and vaporous feed components, exits absorption zone 2 in conduit 4 and passes to stripping zone 5. Stripped vapors, which contain aforementioned absorbed gases, are removed from the rich oil in stripping zone 5 and pass in conduit 6 to cooling zone 17. Feed enters conduit 6 through conduit 1 at a point upstream of the cooling zone such that admixture of feed components and stripped vapor components may take place before their entry into the cooling zone.

A stripped oil stream is withdrawn from stripping zone 5 in conduit 7. A portion of stripped oil exits conduit 7 in conduit 8 and passes to absorption zone 2 as the aforesaid first lean oil. The remaining portion of stripped oil exits conduit 7 in conduit 10 and passes to fractionation zone 11 where this portion of stripped oil is separated into a liquefied hydrocarbon vapor product and a hydrocarbon liquid. The liquefied hydrocarbon vapor product is withdrawn from fractionation zone 11 and exits the process in conduit 14. The hydrocarbon liquid exits fractionation zone 11 in conduit 12. A portion of the hydrocarbon liquid exits conduit 12 in conduit 9, passing as aforesaid second lean oil to absorption zone 2. The remaining portion of the hydrocarbon liquid is withdrawn from conduit 12 in conduit 13 and exits the process as a hydrocarbon liquid product.

DETAILED DESCRIPTION OF THE INVENTION

The refining of petroleum involves numerous processes such as crude oil distillation, catalytic reforming of naphtha, catalytic cracking of residual oils, etc. These processes are well known to those skilled in the art and need not be discussed in great detail herein. However, a characteristic of these processes and many others to be found in petroleum refineries and hydrocarbon processing plants is the production of components which are broadly referred to herein as "normally vaporous hydrocarbons" and "normally liquid hydrocarbons". Normally vaporous hydrocarbons are hydrocarbons which at "normal" conditions of temperature and pressure exist in the vapor state. Conditions referred to in the art as normal conditions are a pressure of 1 atmosphere and a temperature of 60° F. When normally vaporous hydrocarbons are transformed from the vapor state to the liquid state, they are said to become liquefied hydrocarbon vapors. Normally liquid hydrocarbons are those which exist in the liquid state at normal conditions. The present invention broadly provides a method for separating the effluent from any petroleum or hydrocarbon refining or conversion process which contains the types of components which are referred to as normally vaporous and normally liquid hydrocarbons.

For illustrative purposes, the present invention will be described with reference to the effluent from a fluid catalytic cracking process. Normally liquid and normally vaporous hydrocarbons from a fluid catalytic cracking unit conventionally leave in the liquid and vapor streams from the fractionation zone of the unit. These streams are sent to a separation process for recovery of a stabilized liquid hydrocarbon product, or stabilized gasoline, liquefied hydrocarbon vapors and light gases. The stabilized gasoline product principally comprises hydrocarbons having 5 or more carbon atoms per molecule. This gasoline is referred to as stabilized because it does not contain light materials such as ethane or propane or hydrogen which would contribute effervescence to the gasoline. The liquefied hydrocarbon vapor from the separation process typically comprises hydrocarbons having from 2 to 4 carbon atoms per molecule and includes such compounds as propane, butylenes and the like. Liquefied hydrocarbon vapor is commonly referred to in the art as liquefied petroleum gas, or LPG. This product may be further processed in downstream fractionation facilities if it is desired to produce further-purified hydrocarbon product streams such as, for example, a stream substantially comprising hydrocarbons of only 3 carbon atoms. The light gas stream from the separation process commonly contains compounds such as methane and hydrogen. These light components are valuable primarily as fuel and are conducted from the separation process to a fuel system.

In the embodiment of the separation process of my invention shown in the attached drawing a feed composed of an admixture of normally liquid hydrocarbons and normally vaporous hydrocarbons and hydrogen enters the process in conduit 1. A feed of this type has commonly been produced through its vaporization from a liquid phase or from its separation from a two-phase mixture of liquid and vapor. In either case the feed, normally vaporous at its point of origin, may arrive at the separation process as a mixed phase. This will occur, for instance, where the feed at its point of origin occurs at or near dew point conditions and in transmission from the origin to the separation process it is cooled or compressed in some manner. Some prior art separation processes have made use of the liquid portion of the feed as an absorbing fluid for the purpose of furthering the absorption necessary for component separation. While this does improve the efficiency of the process, it falls far short of true optimization. The process of my invention optimizes separation efficiency by treating the feed in a cooling zone to condense as much as is conveniently possible of the readily condensable portions of the feed, thereby providing an increased amount of liquid for use as an absorption medium. The process of my invention further improves upon the prior art by separating liquid and vapor phases from the partially condensed feed and introducing these phases at certain geometrically pre-set locations in an absorption zone. The vapor phase is introduced at the bottom of a vertically-oriented absorption zone in order that the vaporous portion of the feed should traverse upwardly as many contact stages as possible. This is done so that soluble components of the vapor are dissolved into liquid within the absorption zone to the greatest extent possible. The liquid phase is introduced into the absorption zone at a higher elevation so that this liquid, falling through the absorption zone, will pass as many absorption stages as necessary to absorb as much as possible of the vaporous components in the vapor portion of the feed.

Referring again to the drawing, feed entering the process in conduit 1 passes through conduit 6 to cooling zone 17. Cooling zone 17 may be a shell and tube-type heat exchanger or any other of the commonly used apparatuses for contact of condensing vapors with a cooling medium. A cooling medium such as cold water enters conduit 15 and absorbs heat within the cooling zone, exiting thereafter in conduit 16. Withdrawal of heat from the feed will result in its partial condensation, that is heavier components will condense into a liquid phase, leaving lighter components as vapors. The liquid and vapors exit cooling zone 17 in conduit 6 and pass to separation zone 18. A suitable separation zone for use in the process of my invention may be any of the well known separation devices in current use, such as a closed vessel which provides space for disengagement of liquid from vapor and for the accumulation of finite portions of liquid and vapor phases. A vertical or horizontal vessel devoid of internal parts may be found to suffice in most cases. In situations where mist occurs in the vapor phase it may be necessary to provide de-misting means within the vessel, such as a pad of wire mesh through which the vapor must pass. Such de-misting means are well known in the art and they function by providing surfaces for the coalescence of droplets entrained by the vapor.

The vapor phase from the separation zone exits in conduit 19 end passes to the bottom of absorption zone 2. Absorption zone 2 may be one or more vertically disposed plate or packed absorption towers, having a total of 20 or more contact stages. The absorption zone is maintained at conditions selected to absorb at least a portion of the soluble vaporous components of the feed into the liquid within the zone. These conditions include a pressure of from about 150 to 500 psig and a temperature of from about 80° to 150° F. Since absorption is normally exothermic, it may be necessary to provide one or more heat removal means to prevent the temperature within the absorption zone from exceeding these limits. A preferred range of temperature of the effluent streams from absorption zone 2 is 80° to 140° F. The heat removal means can be a system, such as those well known in the art, which removes liquid from an otherwise overheated stage within the absorption zone, pumps this liquid through a cooling device and returns the cooled liquid to the stage immediately below. Liquid flowing downward within the absorption zone, countercurrent to upward-flowing vapors, is provided by streams of lean oil which enter near the top of absorption zone 2 in conduits 8 and 9 and by a stream of liquid withdrawn from the separation zone in conduit 20 and introduced into the absorption zone above the entrance point of feed vapors. Lean oil is referred to as lean because it is substantially less than saturated with vaporous feed components. In flowing downwardly through the absorption zone, the lean oils absorb vaporous feed components and a portion of gaseous feed components. Combined lean oils, absorbed vaporous feed components and liquid feed components exiting absorption zone 2 in conduit 4 are collectively referred to as rich oil. Gases which have not been absorbed by the lean oil are withdrawn from the top of absorption zone 2 in conduit 3. Rich oil withdrawn from absorption zone 2 in conduit 4 is introduced near the top of stripping zone 5.

As was indicated above, it is desired that the hydrogen and methane exit the separation process as gases in conduit 3 and that the ethane, propane, propylene, butanes and butylenes exit the process as liquefied hydrocarbon vapor conduit 14. Ideally, therefore, the rich oil entering stripping zone 5 would contain no hydrogen or methane. However, a portion of the hydrogen and methane in the feed is unavoidably absorbed in the rich oil, and the primary function of the stripping zone is to remove these absorbed gases. Stripping zone 5 may be a conventional, vertically disposed plate or packed tower provided with heat input means to furnish the heat for stripping. Satisfactory heat input means may be a conventional kettle or thermosiphon reboiler or other such device. The stripping tower should preferably have 20 or more contact stages. Feed to the stripping tower preferably enters at or near the top in order that rich oil provides liquid for rectification in all contact stages. Vapor generated through boiling of liquid in the heat input means flows upwardly in the stripping zone and countercurrently contacts the rich oil. The rectification which ensues enriches the vapor in the lighter components such that vapor withdrawn from stripping zone 5 in conduit 6, referred to as stripped vapor, contains substantially all of the hydrogen and methane which entered stripping zone 5 with the rich oil. Because the stripped vapor also contains some heavier materials, it is passed in conduit 6 to cooling zone 17, where it is partially condensed in admixture with feed components. In this manner the heavier materials which have unavoidably been stripped from the rich oil may be recovered, an the gaseous material in the stripped vapor may leave the absorption zone in conduit 3. Rich oil, after being stripped of absorbed gases in stripping zone 5, is referred to as stripped oil and exits stripping zone 5 in conduit 7. This stripped oil is suitable for use as lean oil and is divided into two fractions. One fraction of stripped oil exits conduit 7 in conduit 10 and passes to fractionation zone 11. The remaining fraction of stripped oil exits conduit 7 in conduit 8 and passes as a primary lean oil to absorption zone 2.

Stripped oil entering fractionation zone 11 in conduit 10 is fractionated into an overhead liquid material and a bottoms liquid material. The bottoms liquid material, which is suitable for use as lean oil, exits fractionation zone 11 in conduit 12. A portion of bottoms liquid material exits conduit 12 in conduit 9, and passes to absorption zone 2 for use as a secondary lean oil, secondary in the sense that, chronologically, it is the second lean oil to contact feed vapors rising within the absorption zone. The portion of bottoms material remaining in conduit 12 exits in conduit 13, leaving the process as a stabilized hydrocarbon liquid product. This product principally comprises hydrocarbons having 5 or more carbon atoms. Fractionation zone 11 may be a conventional, vertically oriented, plate or packed fractionation tower, having 25 or more contact stages, and furnished with overhead vapor condensing and reboiler heat input means. Fractionation zone feed preferably enters at or near the middle of the fractionation tower. The fractionation zone also has means for returning a portion of the overhead liquid material (condensed overhead vapor) to the fractionation tower as reflux. The remaining portion of overhead liquid material exits fractionation zone 11 in conduit 14 as a liquefied hydrocarbon vapor product. The liquefied hydrocarbon vapor product may comprise hydrocarbons having 2 to 4 carbon atoms per molecule.

It is to be noted that in the process of my invention, contrary to prior art separation processes, the introduction of heat at the bottoms of the absorption zone is proscribed. I have found that the marginal improvement in removal of gases from the feed which would result from heat-generated vapors at the bottom of the absorption zone is over-shadowed by the increased energy requirement of the process. This is because any heat introduced into the bottom of the absorption zone must only be removed at a higher elevation in order to promote efficient absorption of desired feed vapors.

It should further be noted that in the process of my invention the vapors from the feed enter the absorption zone at the bottom in order that the feed vapors may fully traverse the maximum number of absorption stages. Any other configuration whereby feed vapors are introduced above useful absorption stages is less efficient, since those absorption stages are bypassed by feed vapors.

A still further improvement over the prior art which is provided by the process of my invention is in the pre-set configuration of introduction of feed liquids and feed vapors into the absorption zone. It has been the practice in certain prior art designs to introduce liquid into the absorption zone at a point below the entry of feed vapors. The result is that liquid which would otherwise be useful for absorption falls through the absorption zone without having contacted feed vapors. The process of my invention avoids this prior art defect by introducing all liquids above the point of introduction of feed vapors. The election of the specific point within the absorption zone for the introduction of feed-derived and stripped vapor-derived liquids depends entirely upon the composition existing at the various locations within the absorption zone. Knowing the composition of the feed and stripped vapor liquids and knowing the compositions of liquids existing upon the various absorption stages within the absorption zone, one may readily elect the introduction point. The liquids should be introduced into an absorption stage at a point where their composition most closely resembles the composition of liquids occurring at that stage. The tray-to-tray liquid-vapor equilibrium calculations required to determine the compositions of liquids at the various absorption stages are well within the skills of those versed in the art.

Reasonable variation and modification are possible within the scope of the foregoing disclosure, the drawing and the claims to the invention without departing from the spirit thereof.

I claim as my invention:

1. A process for the recovery of selected hydrocarbon liquid and vapor constituents from a feed stream containing said constituents, which comprises the steps of:
   a. commingling said feed stream with a stripped vapor formed as hereinafter set forth;
   b. cooling the resultant mixture sufficiently to effect partial condensation thereof;
   c. separating the thus cooled mixture into a liquid phase and a vapor phase;
   d. introducing said vapor phase into the lower portion of an absorption zone and introducing said liquid phase to said zone at a higher elevation than the vapor phase;
   e. passing a rich oil from the lowermost point of the absorption zone to a stripping zone and therein stripping absorbed components therefrom;
   f. commingling resultant stripped components with said feed stream as said stripped vapor;
   g. introducing a portion of the stripped oil from the stripping zone to the absorption zone at higher elevation than said liquid phase;
   h. fractionating another portion of the stripped oil from the stripping zone to separate hydrocarbon vapors therefrom; and
   i. supplying at least a portion of the resultant fractionation bottoms to said absorption zone at a higher elevation than the first-mentioned portion of said stripped oil from the stripping zone.

2. The process of claim 1 further characterized in that said fractionation bottoms principally comprises hydrocarbon molecules having 5 or more carbon atoms.

3. The process of claim 1 further characterized in that said feed stream comprises normally liquid and normally vaporous hydrocarbons and hydrogen.

* * * * *